(12) United States Patent
Hilmer et al.

(10) Patent No.: US 7,515,259 B2
(45) Date of Patent: Apr. 7, 2009

(54) FLOW CELL FOR OPTICAL DETECTOR AND METHOD OF FORMING SAME

(75) Inventors: Christian A. Hilmer, Landshut (DE); Jeffrey S. Thompson, Los Gatos, CA (US); Micheal J. McAdams, Los Gatos, CA (US); Angelo Rubero, Jr., Burlingame, CA (US)

(73) Assignee: Dionex Corporation, Sunnyvale, CA (US)

( * ) Notice: Subject to any disclaimer, the term of this patent is extended or adjusted under 35 U.S.C. 154(b) by 263 days.

(21) Appl. No.: 11/373,707

(22) Filed: Mar. 10, 2006

(65) Prior Publication Data

US 2007/0211244 A1   Sep. 13, 2007

(51) Int. Cl.
*G01N 1/10* (2006.01)
(52) U.S. Cl. ..................................... 356/246; 356/440
(58) Field of Classification Search .................. 356/244, 356/246, 432–440
See application file for complete search history.

(56) References Cited

U.S. PATENT DOCUMENTS

| | | | |
|---|---|---|---|
| 3,332,316 A | 7/1967 | Saunders | |
| 3,552,864 A | 1/1971 | Shields | |
| 4,076,420 A * | 2/1978 | De Maeyer et al. | 356/73 |
| 4,575,424 A * | 3/1986 | Allington et al. | 210/198.2 |
| 4,580,901 A | 4/1986 | Goldsmith | |
| 4,588,893 A | 5/1986 | Vidrine et al. | |
| 4,747,687 A | 5/1988 | Hoppe et al. | |
| 4,886,356 A | 12/1989 | Paradis | |
| 5,003,174 A | 3/1991 | Datwyler et al. | |
| 5,139,333 A | 8/1992 | Reinhard | |
| 5,814,742 A | 9/1998 | Vissers et al. | |
| 5,905,271 A | 5/1999 | Wynn | |
| 6,122,049 A | 9/2000 | Sugiyama et al. | |
| 6,188,813 B1 | 2/2001 | Dourdeville et al. | |
| 6,200,531 B1 * | 3/2001 | Liljestrand et al. | 422/52 |
| 6,526,188 B2 | 2/2003 | Dourdeville et al. | |
| 6,587,195 B1 | 7/2003 | Jennings | |
| 6,747,740 B1 | 6/2004 | Leveille et al. | |
| 6,867,857 B2 | 3/2005 | Hobbs | |

(Continued)

OTHER PUBLICATIONS

Barka, G., Wege zur Miniaturisierung von Analysensystemen, Tiel 3: Automatische Probeninjektion, *LaborPraxis*, Nov. 1997.

(Continued)

*Primary Examiner*—Hoa Q Pham
(74) *Attorney, Agent, or Firm*—Morgan, Lewis & Bockius LLP; Victor E. Johnson; David J. Brezner

(57) ABSTRACT

A flow cell for optical detector includes a flow cell body, a face-seal window, and a pressed illumination window. The flow cell body is formed of an inert material and includes large and small bores, and inlet and outlet passageways in fluid communication with the small bore. The face-seal window is affixed within the large area aperture to form a liquid tight seal, while the pressed illumination window is press-set into the small bore. The pressed illumination window is spaced away from the face-seal window to form a sample chamber having a pathlength distance γ. The face-seal window and the pressed window provide an optical path through the sample chamber. Preferably, the flow cell body is formed of PEEK. Methods of forming and using the flow cell are also disclosed.

32 Claims, 6 Drawing Sheets

U.S. PATENT DOCUMENTS

| | | |
|---|---|---|
| 2002/0038998 A1* | 4/2002 | Fujita et al. ............ 313/495 |
| 2004/0027568 A1 | 2/2004 | Maiefski et al. |
| 2004/0036987 A1 | 2/2004 | Wisecarver et al. |
| 2004/0066509 A1 | 4/2004 | Canty et al. |
| 2004/0080744 A1 | 4/2004 | Hobbs |
| 2007/0064226 A1* | 3/2007 | Kolp et al. ............ 356/246 |

OTHER PUBLICATIONS

Dionex Corporation, PDA-100 (USB) Photodiode Array Detector Operator's Manual, Revision 03, Mar. 2006, 132 pp.

Dionex Corporation, UVD 170U and UVD 340U UV/VIS Detectors Operating Instructions, Revision 1.0-a, Jul. 2003, 54pp.

van der Vlis, E., Development of a needle device for on-line electroextraction-liquid chromatography. *J. Chromatogr. A.* 741: 13-21 (1996).

Vissers, J. et al., A fully automated microautosampler for micro and capillary liquid chromatography, *International Laboratory*, Jan. 1996.

* cited by examiner

FLOW CELL FOR OPTICAL DETECTOR AND METHOD OF FORMING SAME

BACKGROUND OF THE INVENTION

1. Field of the Invention

This invention relates, in general, to flow cells for optical detectors, and more particularly to flow cells for chromatography systems, as well as methods for their manufacture and use.

2. Description of Related Art

Absorbance detectors are utilized in a wide variety of analysis applications including, but not limited to, high pressure liquid chromatography and ion chromatography. Generally, absorbance detectors have a flow cell through which sample flow is directed between two windows. Light is directed through the windows and sensed to determine the amount of light absorbed by the sample flowing between the windows. Typically, absorbance detectors have a linear range of about five orders of magnitude.

The typical flow cell has a pathlength of about 10 mm in length. However, samples coming from chromatography columns and other analytical equipment often are of sufficiently large concentration that the linear range of the optical detector is exceeded with a 10 mm pathlength cell. Thus, a cell with a shorter pathlength is required. The desired pathlength is in the 0.05-0.4 mm range in order to analyze concentrated samples, such as those exiting semi-prep chromatography columns, without exceeding the linear range of the optical detector. Such a small pathlength however, is typically on the order of, or shorter than, the diameter of the passageways that bring the sample flow into and out of conventional flow cells. As such, the configuration of conventional flow cells generally results with unswept volume, that is, volumes or spaces within the sample chamber of the flow cell in which sample flow may not reliably flow and instead may remain stagnant.

In addition, conventional flow cells typically utilize o-rings, gaskets, stepped lenses, and/or other sealing means in order to provide a liquid-tight seal between the windows and the cell body. Generally, such sealing means are applied some distance away from the pathlength in the sample chamber and results with a configuration having unswept volume.

What is needed is an improved flow cell which overcomes the above and other disadvantages of known flow cells.

BRIEF SUMMARY OF THE INVENTION

In summary, one aspect of the present invention is directed to a flow cell for an optical detector including a flow cell body formed of an inert material and including a large area aperture and a small area aperture, and inlet and outlet passageways in fluid communication with the small area aperture, a face-seal window affixed within the large area aperture to form a liquid tight seal, and a pressed window press-set into the small area aperture and spaced away from the face-seal window a pathlength distance $\gamma$ thereby forming a sample chamber between the face-seal window and the pressed window. The face-seal window and the pressed window provide an optical path through the sample chamber.

In one embodiment, the inert material may be plastic, and/or the inert material may be a polyetheretherketone. The liquid-tight seal may withstand 1500 psi static pressure. The inlet and outlet passageways have a minimum inner dimension, and wherein a distance separating the pressed window from the face-seal window may be less than the minimum inner dimension of said passageways.

In one embodiment, the pressed window has a diameter $\Phi$, and the flow cell has an illuminated volume V substantially equal to $\gamma^{.574} \pi*(\Phi/2)^2$. The illuminated volume V may be less than approximately 0.7 μL.

In one embodiment, both windows are lenses having inner surfaces which are flat and parallel to one another.

The large area aperture may be a large diameter bore and the small area aperture may be a small diameter bore. The sample chamber may be formed by a portion of the small diameter bore. The flow cell may further include inlet and outlet pockets extending along a side wall of the small diameter bore respectively interconnecting the inlet and outlet passageways with the sample chamber. The flow cell body may include an illumination aperture near the pressed window at the end of the window opposite from the sample chamber. The flow cell body may include a mounting bore extending outwardly from the large diameter bore. The flow cell may further include a retainer received within the mounting bore for removably affixing the face-seal window within the large diameter bore. The retainer may threadably engage the mounting bore. The retainer may include a viewing aperture extending therethrough, the viewing aperture being colinear with the pressed window and the face-seal window. The flow cell may alternately include an external plate for removably affixing the face seal window or lens within the large diameter bore.

The flow cell of the present invention may be utilized in a chromatography system including an absorbance detector for detecting absorbance of a sample. Similarly, the flow cell of the present invention may be used to analyze a sample by providing an optical analysis system having an absorbance detector including the flow cell of the present invention, filling the sample chamber with a sample, directing light of a known wavelength through the pressed window and the face-seal window, and detecting absorbance of light by the sample within the sample chamber. The filling step may include flowing sample through the sample chamber at a rate of approximately 100 mL per minute.

Another aspect of the present invention is directed to a method of forming a flow cell, the method including the steps: providing a flow cell body formed of an inert material, the flow cell body including large and small area apertures, and inlet and outlet passageways in fluid communication with the small area aperture, wherein the large area aperture has a bottom; press-setting a pressed window into the small area aperture to form a first liquid-tight seal, wherein the pressed window is press-set into the small area aperture a distance away from bottom of the large area aperture a distance D; and affixing a face-seal window into the large area aperture, wherein the pressed window and the face-seal window provide an optical path through the flow cell body of the flow cell and define a sample chamber therebetween having a pathlength distance $\gamma$ substantially equal to distance D.

In one embodiment, the providing step may include forming the flow cell body of polyetheretherketone. The method may further include the step of utilizing a stepped press setting fixture to press-set the pressed window or lens the distance D. The inserting step may include press-setting the pressed window into the small area aperture through the large area aperture. The inlet and outlet passageways have a minimum inner dimension, and wherein the distance $\gamma$ may be less than the minimum inner dimension of said passageways. The providing step may include providing the flow cell body with an illumination aperture near the pressed window or lens at the end of the window opposite from the sample chamber. The providing step may include providing the flow cell body with a mounting bore extending outwardly from the large area aperture. The providing step may include providing a retainer received within the large diameter portion for removably affixing the face-seal within the large area aperture. The affixing step may include threadably engaging the retainer within the large area aperture.

The flow cell and methods of the present invention have other features and advantages which will be apparent from or are set forth in more detail in the accompanying drawings, which are incorporated in and form a part of this specification, and the following Detailed Description of the Invention, which together serve to explain the principles of the present invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Generally, the flow cell of the present invention employs a unique combination of materials and geometry to provide a flow cell design that allows for small pathlengths while minimizing unswept volume. The flow cell design provides for high fluid pressures in the sample chamber. The flow cell of the present invention also allows for simply adjusting the pathlength at the time of assembly while using conventional machining techniques and simple lens components.

Figure 1:
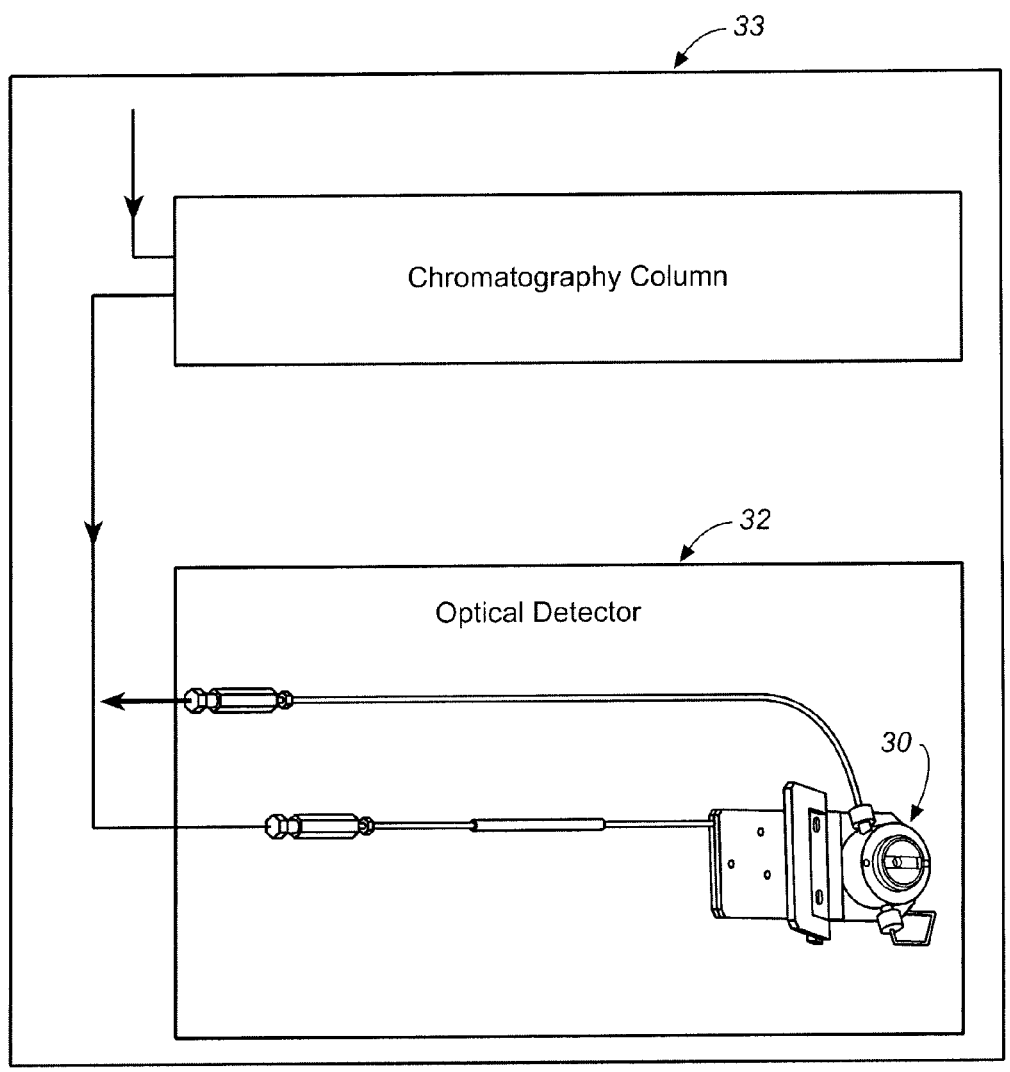
FIG. 1 is a schematic view of a chromatography system incorporating an optical detector having a flow cell in accordance with the present invention.

Turning now to the drawings, wherein like components are designated by like reference numerals throughout the various figures, attention is directed to FIG. 1, which illustrates a flow cell 30 for an optical detector 32 that is used in a high-performance liquid chromatography (HPLC) system 33 in accordance with the present invention. One will appreciate that the flow cell and the optical detector may be used in conjuction with other analytical applications in which absorbance, flourescence, and/or other photometric properties of samples are detected and analyzed, including, but not limited to, ion chromatograpy and mass spectrometry. For example, the flow cell of the present invention may be incorporated into the PDA-100 Photodiode Array Detector, provided by Dionex Corporation of Sunnyvale, Calif. The operation and use of the PDA Photodiode Array Detector is described in depth in the PDA-100 (USB) PHOTODIODE ARRAY DETECTOR OPERATOR'S MANUAL (Document No. 031898, Revision 03, Mar. 2006), the entire contents of which is incorporated herein by this reference. One will appreciate that the flow cell of the present invention may also be incorporated into other devices utilizing a optical flow cell.

Figure 2:
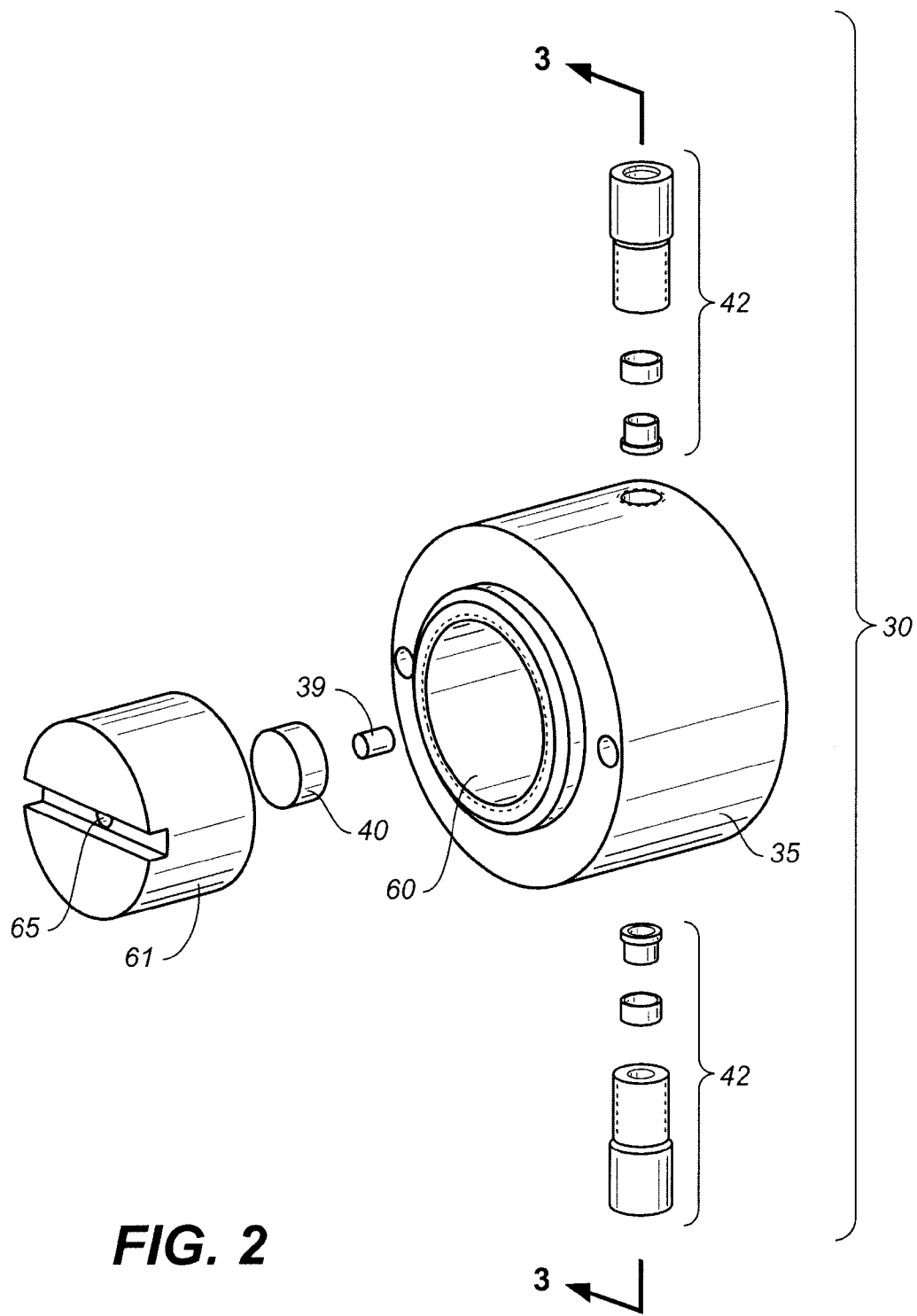
FIG. 2 is an enlarged, exploded perspective view of the flow cell of FIG. 1.
Figure 3:
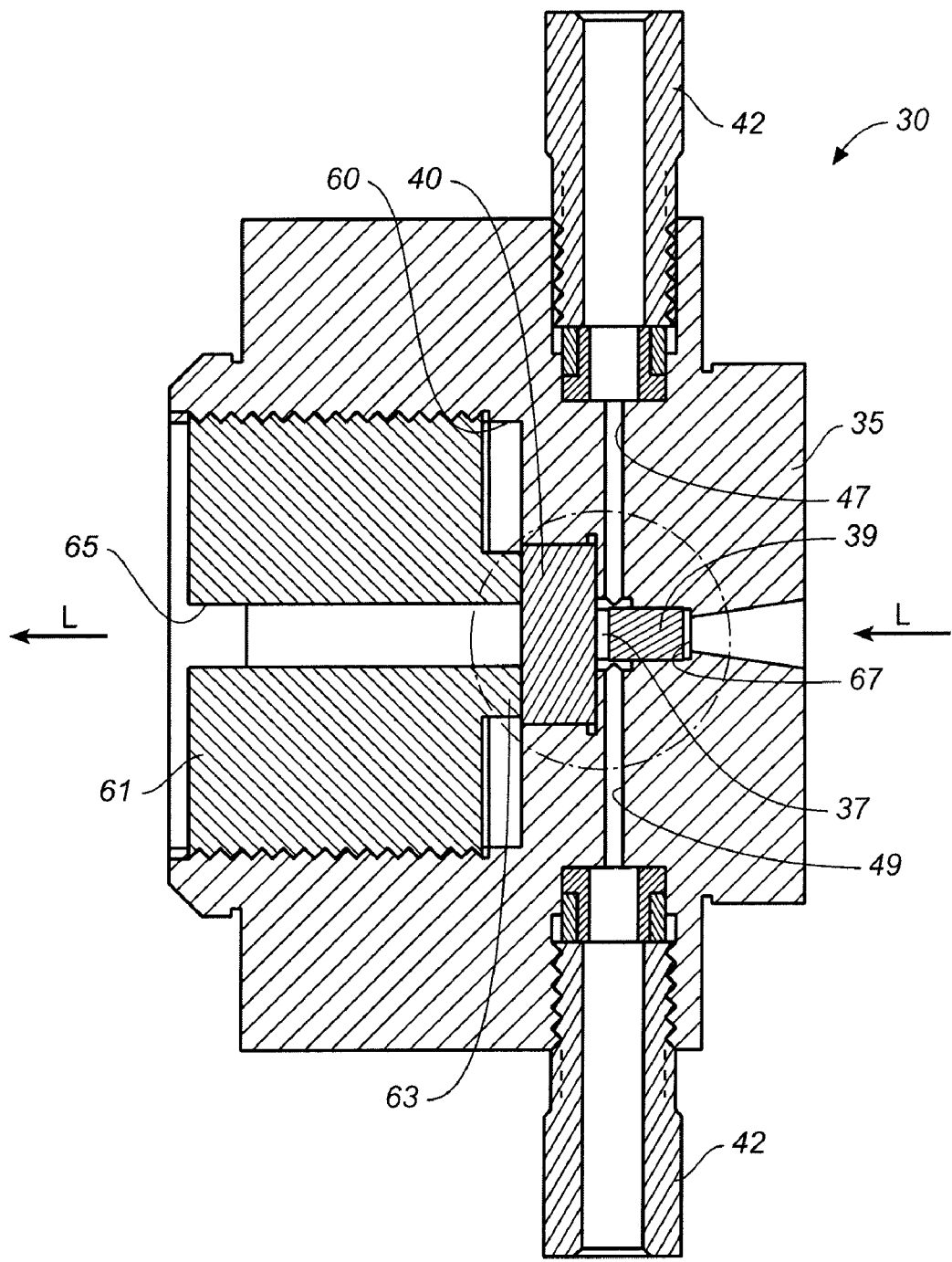
FIG. 3 is a cross-sectional assembly view of the flow cell of FIG. 1 taken substantially along line 3-3 in FIG. 2.

With reference to FIG. 2 and FIG. 3, flow cell 30 generally includes a flow cell body 35 having a sample chamber 37 (see FIG. 3 and FIG. 4), and a pair of windows collinearly aligned with the sample chamber such that light may be directed along an optical path through the sample chamber. In the present invention, light enters the flow cell body through an illumination window 39 and exits through a face-seal window 40, as indicated by arrows L in FIG. 3. One will appreciate that the configuration of the flow cell may vary, and that in some embodiments, light may travel in the opposite direction entering window 40 and exiting window 39.

In the present invention, flow cell body 35 is preferably monolithically formed of an inert material that is suitable for the applications in which it is used. Namely, the flow cell is made of a material that is substantially non-reactive with the samples, eluents, reagents and other liquids and materials that will be directed through flow cell 30 and detected by optical detector 32. Also, the flow cell body is formed of a material that provides sufficient structural integrity to serve as a structural base to mechanically receive and support the various components of the flow cell, such as tubing fittings 42, windows 39 and 40, and window retainer 61.

In one embodiment, the flow cell body is formed of a polyetheretherketone (PEEK), which is particularly well suited because it is an inert material with sufficient structural integrity to be threaded and otherwise machined, the reasons for which will become evident below. One will appreciate that other inert materials may be utilized including other polyketones, other inert plastics, and other suitable materials including, but not limited to, the TEFLON family of polymers such as PolyTetraFluoroEthylene (PTFE) and PerFluoroAlkoxy polymer (PFA) and Fluorinated Ethylene Propylene (FEP), TEFZEL or Ethylene TetraFluoroEthylene (ETFE), KEL-F or PolyChloroTriFluoroEthylene (PCTFE), poly methyl pentene (TPX), Ultra High Molecular Weight polyethylene (UHMWPE), Polypropylene, Polyphenylene Sulfide (PPS), polyimide, a variety of Liquid Crystal Polymers (LCP), and other inert polymers. These materials will have varying degrees of structural integrity and more or less chemical compatibility with the samples, eluents and reagents to be used. One will also appreciate that the flow cell body need not be monolithically formed. Instead, the flow cell body may have a core, or other portions thereof, formed of a rigid material provided that all "wetted" portions of the flow cell body are covered and enclosed by an inert material. As will become evident below, however, there are certain advantages to monolithically forming the flow cell body with a machinable inert material such as PEEK.

Figure 6:
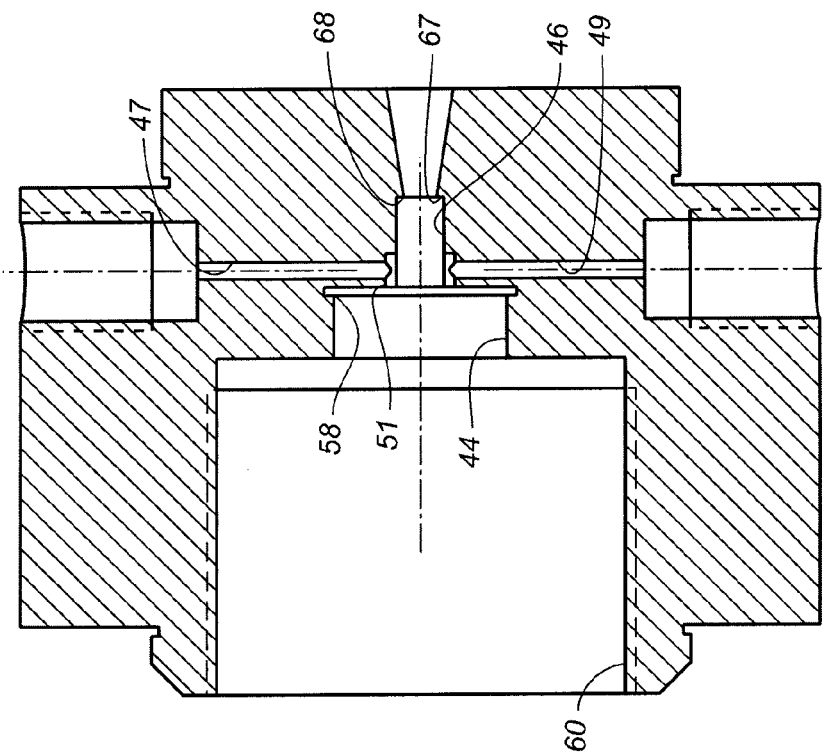
FIG. 6 is a cross-sectional view of the flow cell body of FIG. 1 taken substantially along line 6-6 of FIG. 5.

As shown in FIG. 3 and FIG. 6, flow cell body 35 includes a large area aperture 44 and a small area aperture 46 which are dimensioned to receive and seat face-seal window 40 and illumination window 39, respectively. In the illustrated embodiments, the large and small area apertures are relatively large and small bores, and for the purposes of the present specification, the terms "large area aperture 44" and "large bore 44" are interchangeable, as are the terms "small area aperture 46" and "small bore 46". Cylindrical bores are preferred as they may be simply formed by drilling/boring the flow cell body. Nonetheless, one will appreciate that the apertures (and windows) may have other geometric shapes. For example, the large area aperture (and/or the face-seal window) may have a circular, oval, square or rectangular profile.

The flow cell body also includes an inlet passageway 47 and an outlet passageway 49 in fluid communication with the sample chamber. The volume between the windows largely defines sample chamber 37, and the distance D between the illumination window 39 and face-seal window 40 defines a pathlength distance γ of the flow cell.

In the illustrated embodiment, the windows are fused silica windows. One will appreciate that the windows may be formed of other suitable materials such as glass, sapphire, or other optical materials with various performance characteristics suited for the application. One will appreciate that the windows may be lenses which change the focus of light entering and exiting the flow cell. For example, in the embodiment shown in FIG. 7, illumination window 39' is a lens which will change the focus of light entering the flow cell. One will also appreciate that the face-seal window may be a lens, and that both the illumination window and the face-seal may be lenses. One will also appreciate that the lenses may be of any type, focal length, and diameter compatible with pressing the lens into the small area aperture and/or affixing the lens into the large area aperture, including, but not limited to cylindrical lenses, drum lenses, or aspheric lenses. Preferably, the lenses have inner surfaces that are flat and parallel to one another. Alternatively, the inner surfaces may be concentric spherical surfaces, or concentric cylindrical surfaces. Further still, one or both windows may be drum lenses with an outer spherical surface, or an outer cylindrical surface.

Face-seal window 40 is affixed within large area aperture 44 and seated against a seating surface 51 in an otherwise conventional manner to form a liquid tight seal. In contrast, illumination window 39 is press-set into the small area aperture. For the purposes of the present invention, the illumination window may also be referred to below as the "pressed" window.

The press-set configuration of the illumination window or lens is particularly advantageous, not only because it allows for a simplified design capable of withstanding high fluid pressures, but also because it allows for a simplified manner of adjustably setting the position of the illumination window within the flow cell body and relative to the face-seal window. Accordingly, the press-set configuration of the illumination window allows for easily and adjustably setting the pathlength distance γ of sample chamber 37 and thus the pathlength of the flow cell. Moreover, the press-set configuration allows for a variety of pathlengths utilizing the same components.

Figure 4:
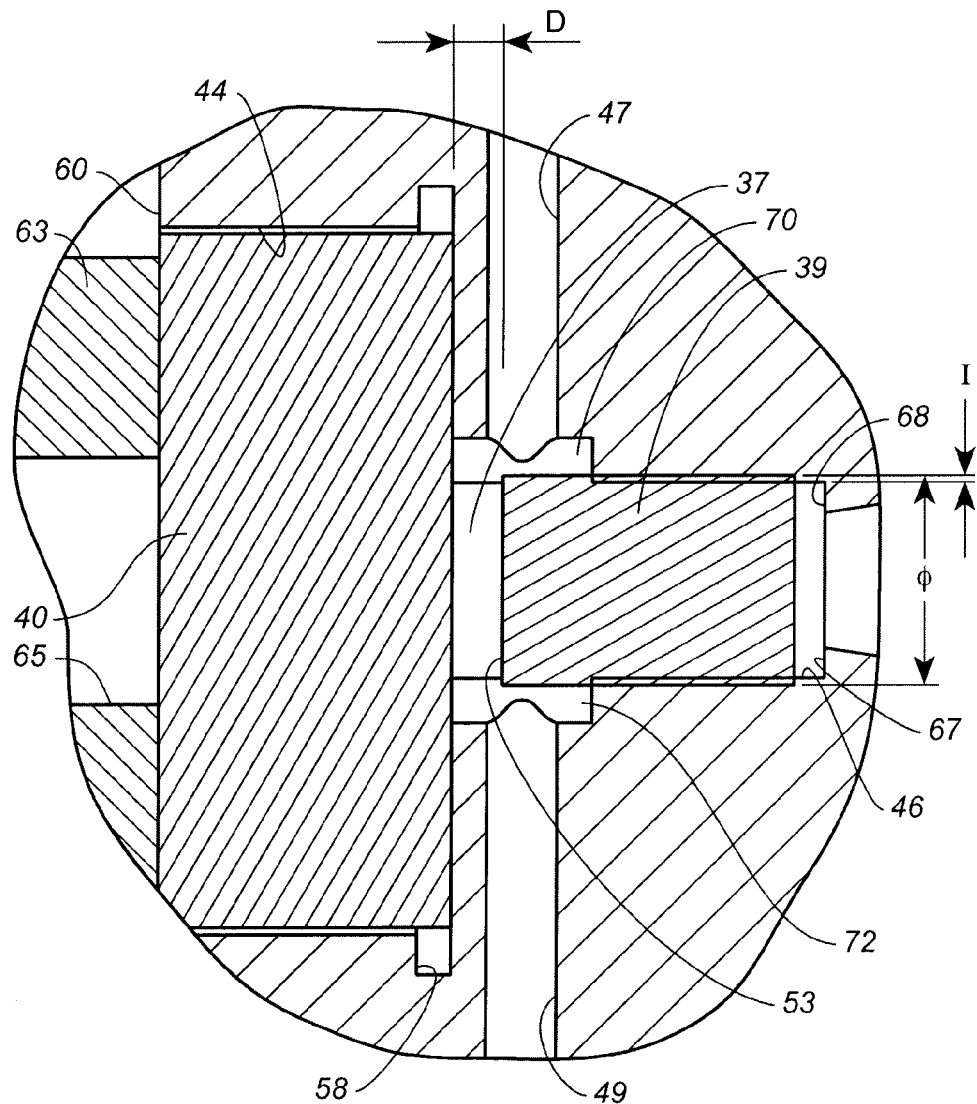
FIG. 4 is an enlarged detail of FIG. 3 showing a sample chamber of the flow cell of FIG. 1.

With reference to FIG. 4, small bore 46 has an inner diameter of approximately 1.5 mm bore. Illumination window 39 is pressed therein to a desired depth such that an internal surface 53 of the illumination window is spaced from seating surface 51 the desired distance D. One will appreciate that the actual depth at which the illumination window is set into small bore 46 determines the distance D and thus pathlength γ of flow cell 30.

Figure 7:
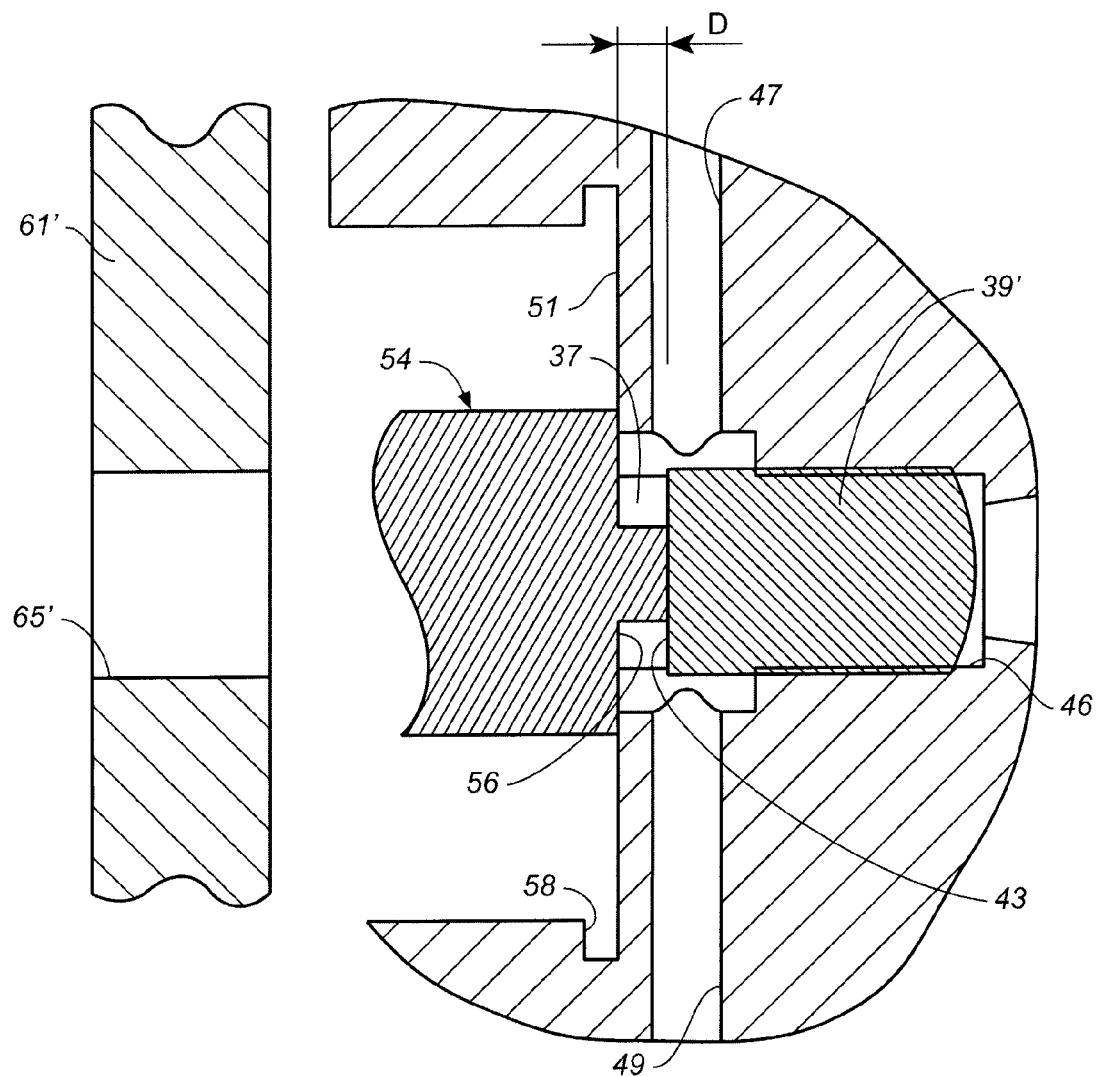
FIG. 7 is an enlarged detail of FIG. 1 similar to FIG. 4 but showing installation of a window using a stepped press setting fixture to press-set the pressed window the distance D.

In order to precisely set the depth and position of the internal surface of the illumination window or lens, a stepped press setting fixture 54 may be used to push illumination window 39 into place. The stepped press setting fixture indexes the relative position of the internal surface of the illumination window with respect to seating surface 51 of large bore 44, as shown in FIG. 7. In particular, the stepped press setting fixture includes a stepped shoulder 56 that abuts against the seating surface once the desired distance D has been achieved. Stepped press setting fixtures having different tool lengths may be used to set different pathlengths during assembly.

The outer diameter of the illumination window is larger than the inner diameter of the small bore in order to provide a liquid-tight interference fit between illumination window 39 and flow cell body 35. Also, the length to diameter ratio of the illumination window is such to allow the interference fit to obtain a high pressure seal, one that is capable of withstanding fluid pressures in the sample chamber in excess of approximately 500 psi, more preferably in excess of approximately 1000 psi, and most preferably in excess of approximately 1500 psi. Thus, the press-fit configuration of the present invention allows for a high-pressure seal to be formed without the use of seal materials such as o-rings, gaskets and other sealing means which can contaminate the flow path or introduce unswept volume. Moreover, such configuration results in a flow cell in which only the flow cell body and the windows are wetted.

In the present invention, the outer diameter of the illumination window is approximately 1.5 mm and the length is approximately 2 mm. When using a PEEK flow cell body and a fused silica illumination window, such dimensions have provided a fluid tight seal capable of withstanding 1500 psi static pressure, with a pressure loss of less than 100 psi after 15 minutes. One will appreciate that the actual interference dimensions between illumination window 39 and small bore 46 may vary depending upon the materials and size of the flow cell body and the illumination window. In the present invention, the outer diameter of the illumination window is approximately 0.04 mm larger than the diameter of the bore in the cell body it is being pressed into.

Turning now to the configuration of the face-seal window or lens, large diameter bore 44 includes an undercut 58 to allow face-seal window 40 to seat and abut directly against seating surface 51. Flow cell body 35 includes a mounting bore 60 that extends outwardly from and provides access to the large diameter bore. A retainer 61 is threadably received within the mounting bore to facilitate installation and removal of the face-seal window into and from the large diameter bore. In the illustrated embodiment, the retainer is formed of PEEK, however, one will appreciate that the retainer may also be made of other suitable materials. Also, as the retainer does not have any wetted surfaces and thus it is not essential that the retainer be formed of inert materials. Nonetheless, PEEK is a material that is particularly well-suited for the retainer due to its machine-ability and due to the fact that it will not inadvertently contaminate the internal surfaces of the flow cell, nor generate particulate that may do so. One will appreciate that the face seal window or lens could also be removably affixed to the mounting bore using other suitable means such as an external plate (see, e.g., retainer plate 61', as shown in FIG. 7).

To affix face-seal window or lens 40 within flow cell body 35, the face-seal window or lens is inserted into large diameter bore 44. Next, the retainer is threaded into the mounting bore such that a protrusion 63 abuts against the face-seal window and biases the face-seal window against sealing surface 51. In the illustrated embodiment, the protrusion includes an outer diameter that is slightly less than the outer diameter of the face-seal window thereby facilitating a substantially uniform biasing force that will seat the window against the sealing surface. The retainer is sufficiently tightly threaded to provide enough force against the face-seal window and thus provide a liquid-tight seal between face-seal window 40 and sealing surface 51. In the present embodiment, the inherent resilience of the PEEK flow cell body is particularly well suited to provide a liquid-tight seal between the PEEK flow cell body and the fused silica face-seal window that is capable of withstanding forces of 1500 psi static pressure.

As can be seen in FIG. 3, retainer 61 includes a viewing aperture 65 extending therethrough that is colinear and substantially concentric with the windows. Similarly, flow cell body 35 includes an illumination aperture 67 near the pressed window at the end of the window opposite from the sample chamber that is also colinear and substantially concentric with the windows. Together, the viewing and illumination apertures provide external access to the windows and thereby provide an optical path through the flow cell body.

With reference to FIG. 4 and FIG. 6, illumination aperture 67 is smaller than the small diameter bore 46 and thus forms an internal shoulder 68 which limits the amount that illumination window 39 may be inserted into the small diameter bore. Internal shoulder 68 also forms the illumination aperture that limits the diameter of illumination entering the cell and keeps the light away from the bore/window boundary. Such configuration may be advantageous in that it may serve as a safety measure preventing the illumination window from being pushed out of the cell body under high pressures in the event of failure. In such embodiments, the illumination window must be installed through the large diameter bore. This is the preferred method of installation as it allows one to easily gauge the position of the illumination window with respect to seating surface 51 and thus easily set the pathlength γ between the illumination window and face-seal window 40. One will appreciate, however, that such a shoulder is not an essential feature. Instead, the illumination aperture may be larger than the small diameter bore, in which case, the illumination window may be installed therethrough. Nonetheless, in some embodiments an illumination aperture smaller than the illumination window is preferred so that the illumination aperture limits the amount of light going through the flow cell to prevent detector sensor saturation.

Turning now to the sample chamber, the configuration of the flow cell of the present invention is particularly advantageous because it provides for a sample chamber that may have pathlengths γ that are smaller than the inlet and outlet passageways of the flow cell body. Also, this configuration provides for minimizing the unswept volume of the sample chamber.

Sample chamber 37 is defined by a portion of small bore 46, namely, the portion of the small bore between internal surface 53 of illumination window 39 and the adjacent exposed surface of face-seal window 40. As can be seen, the pathlength γ of the flow cell is defined by the distance D between the windows and, as noted above, the pathlength γ is simply defined by the position of the illumination window within the small bore. Accordingly, the present invention allows one to set the pathlength of the flow cell during assembly anywhere in the range of approximately 0.01 mm to several millimeters, and preferably in the range of approximately 0.02 mm to 0.8 mm. One will appreciate that the actual range of pathlengths may vary depending upon the overall dimensions of the flow cell body and the small diameter bore.

The configuration of the present invention allows for pathlengths γ that are significantly less than the inner diameters of the inlet and outlet passageways of the flow cell. In the illustrated embodiment, the inner and outer passageways 47 and 49 have inner diameters of approximately 0.5 mm, and the distance D (and thus pathlength γ) is approximately 0.4 mm. As such, one will appreciate that the pathlength γ of flow cell 30 may be orders of magnitude smaller than the dimensions of the inlet and outlet passageways, essentially limited only by the tolerances of the sealing surface and the precision of the stepped press setting fixture.

The configuration of the present invention also allows for an illumination volume of the flow cell that is substantially equal to the pathlength γ multiplied by the internal surface area of the illumination window. In particular, illumination window 39 has a diameter Φ, thereby providing a flow cell illuminated volume V substantially equal to pathlength γ multiplied by the cross-sectional area of the illumination window, as follows:

$$V=\gamma*(\pi*(\Phi/2)^2).$$  Eq. (a)

In the present invention, flow cell 30 has an illuminated volume V approximately 0.7 μL.

Despite the relatively small illuminated volume the flow cell is capable of handling flow rates of approximately 1-100 mL/min.

In order to facilitate fluid flow into the sample chamber, and thus flow rate, inlet and outlet connection pockets 70 and 72 are provided interconnecting the sample chamber with the inlet and outlet passageways 47 and 49, respectively.

Figure 5:
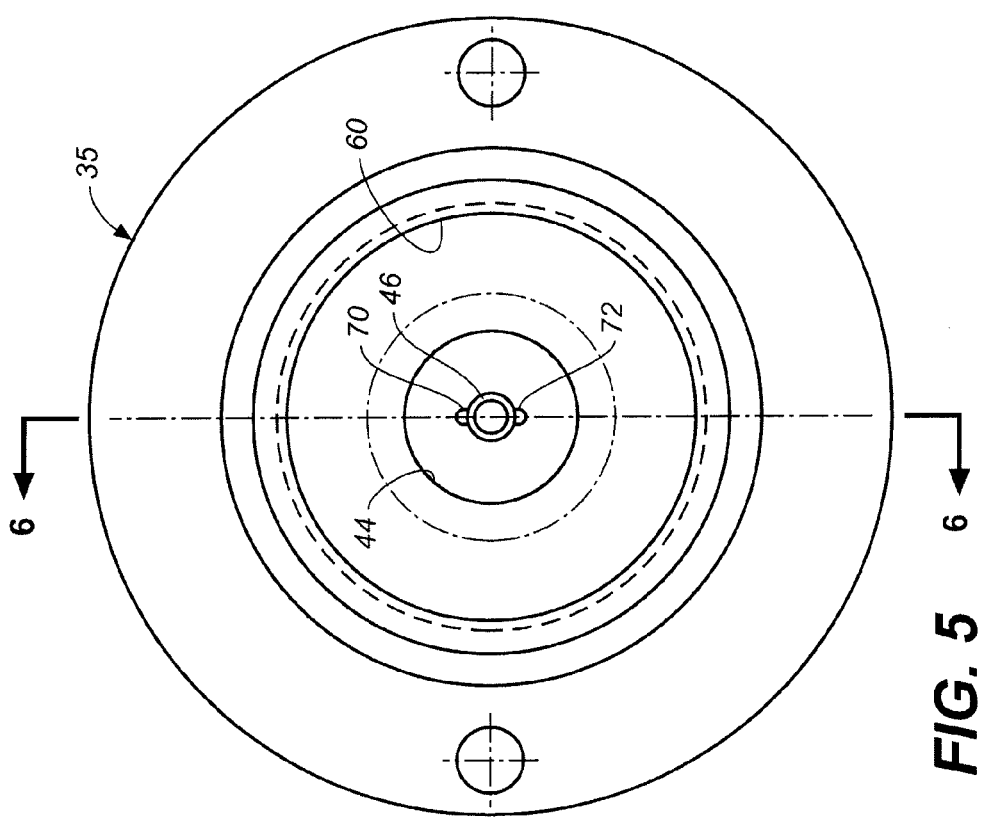
FIG. 5 is a side view of a body of a flow cell body of FIG. 1.

As is evident from FIG. 3 and FIG. 5, all of the fluid flow moves through the pathlength illumination volume of the sample chamber thereby minimizing unswept volume of the flow cell. As there are no voids, recesses, or protrusions within the sample chamber, there is virtually no unswept volume in the flow cell.

Advantageously, the flow cell of the present invention allows for a short pathlength configuration using cell common lens elements and conventional machining techniques. Moreover, the flow cell of the present invention provides for an adjustable flow cell configuration using such common lens elements and conventional machining techniques.

Another advantage of the flow cell of the present invention is that all of the sample carrying fluid flows through the pathlength and the illuminated volume of the flow cell. The configuration of the present flow cell minimizes unswept volume as compared to prior flow cells.

The flow cell of the present invention also allows for configurations which are capable of withstanding flow pressures up to 1500 psi, without the use of discrete seal materials such as O-rings, gaskets, and other sealing means. Advantageously, only the cell body and the windows of the present flow cell are wetted during operation.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A flow cell for an optical detector, said flow cell comprising:

a flow cell body formed of an inert material, the flow cell body including a large area aperture and a small area aperture, the flow cell body also including inlet and outlet passageways in fluid communication with the small area aperture;

a face-seal window affixed within the large area aperture to form a first liquid tight seal; and a pressed window press-set into the small area aperture to form a second liquid tight seal within the small area aperture and spaced away from the face-seal window a pathlength distance γ thereby forming a sample chamber between the face-seal window and the pressed window; and wherein the face-seal window and the pressed window provide an optical path through the sample chamber.

2. A flow cell according to claim 1, wherein the inert material is plastic.

3. A flow cell according to claim 2, wherein the inert material is a polyetheretherketone.

4. A flow cell according to claim 1, wherein the liquid-tight seals withstand 1500 psi static pressure.

5. A flow cell according to claim 1, wherein at least one of the face-seal window and the pressed window is a lens to change the optical focus of light entering and/or exiting the cell.

6. A flow cell according to claim 1, wherein both of the face-seal window and the pressed window are lenses having inner surfaces that are flat and are oriented parallel to one another.

7. A flow cell according to claim 1, wherein the inlet and outlet passageways have a minimum inner dimension, and wherein a distance separating the pressed window from the face-seal window is less than the minimum inner dimension of said passageways.

8. A flow cell according to claim 7, wherein the distance separating the pressed window from the face-seal window defines a pathlength distance $\gamma$, and the pressed window has a diameter $\Phi$; and
wherein the flow cell has an illuminated volume V substantially equal to $\gamma*\pi*(\Phi/2)^2$.

9. A flow cell according to claim 8, wherein the illuminated volume V is less than approximately 0.7 µL.

10. A flow cell according to claim 1, wherein the large area aperture is a large diameter bore and the small area aperture is a small diameter bore.

11. A flow cell according to claim 10, wherein the sample chamber is formed by a portion of the small diameter bore.

12. A flow cell according to claim 11, further comprising inlet and outlet pockets extending along a side wall of the small diameter bore respectively interconnecting the inlet and outlet passageways with the sample chamber.

13. A flow cell according to claim 10, wherein the flow cell body includes an illumination aperture extending outwardly from the small diameter bore.

14. A flow cell according to claim 10, wherein the flow cell body includes a mounting bore extending outwardly from the large diameter bore.

15. A flow cell according to claim 14, further comprising a retainer received within the mounting bore for removably affixing the face-seal window within the large diameter bore.

16. A flow cell according to claim 15, wherein the retainer threadably engages the mounting bore.

17. A flow cell according to claim 15, wherein the retainer includes a viewing aperture extending therethrough, the viewing aperture being colinear with the pressed window and the face-seal window.

18. A flow cell according to claim 14, wherein the face seal window is removably affixed within the large diameter bore by an external plate.

19. In combination, a chromatography system including an absorbance detector for detecting absorbance of a sample, the absorbance detector comprising the flow cell of claim 1.

20. A method of optically analyzing a sample, the method comprising the steps:
providing an optical analysis system having an absorbance detector that includes the flow cell of claim 1;
filling the sample chamber with a sample;
directing light of a known wavelength through the pressed window and the face-seal window; and
detecting absorbance of light by the sample within the sample chamber.

21. The method according to claim 20, wherein the filling step includes flowing sample through the sample chamber at a rate of 100 ml/min per minute.

22. A flow cell according to claim 1, wherein the sample chamber comprises two side walls, a first wall defined by a surface of the face-seal window and a second wall defined by a surface of the pressed window.

23. A method of forming a flow cell, the method comprising the steps:
providing a flow cell body formed of an inert material, the flow cell body including large and small area apertures, and inlet and outlet passageways in fluid communication with the small area aperture, wherein the large area aperture has a bottom;
press-setting a pressed window into the small area aperture to form a liquid-tight seal therein, wherein the pressed window is press-set into the small area aperture a distance away from bottom of the large area aperture a distance D; and
affixing a face-seal window into the large area aperture, wherein the pressed window and the face-seal window provide an optical path through the flow cell body of the flow cell and define a sample chamber therebetween having a pathlength distance $\gamma$ substantially equal to distance D.

24. A method according to claim 23, wherein the providing step includes forming the flow cell body of polyetheretherketone.

25. A method according to claim 23, the method further comprising the step:
utilizing a stepped press setting fixture to determine the distance D.

26. A method according to claim 23, wherein the inserting step includes press-setting the pressed window into the small area aperture through the large area aperture.

27. A method according to claim 26, wherein the inlet and outlet passageways have a minimum inner dimension, and wherein the distance $\gamma$ is less than the minimum inner dimension of said passageways.

28. A method according to claim 23, wherein the providing step includes providing the flow cell body with an illumination aperture extending outwardly from the small area aperture.

29. A method according to claim 23, wherein the providing step includes providing the flow cell body with a mounting bore extending outwardly from the large area aperture.

30. A method according to claim 29, wherein the providing step includes providing a retainer received within the large diameter portion for removably affixing the face-seal within the large area aperture.

31. A method according to claim 30, wherein the affixing step includes threadably engaging the retainer within the large area aperture.

32. A method according to claim 23, wherein the sample chamber comprises two side walls, a first wall defined by a surface of the face-seal window and a second wall defined by a surface of the pressed window.

* * * * *

UNITED STATES PATENT AND TRADEMARK OFFICE
CERTIFICATE OF CORRECTION

PATENT NO.        : 7,515,259 B2                                              Page 1 of 1
APPLICATION NO.   : 11/373707
DATED             : April 7, 2009
INVENTOR(S)       : Christian A. Hilmer et al.

It is certified that error appears in the above-identified patent and that said Letters Patent is hereby corrected as shown below:

Title Page should read

(75) Inventors: Christian A. Hilmer, Landshut (DE); Jeffrey S. Thompson, Los Gatos, CA (US); Michael J. McAdams, Los Gatos, CA (US); Angelo Rubero, Jr., Burlingame, CA (US)

Signed and Sealed this

Fourth Day of August, 2009

JOHN DOLL
*Acting Director of the United States Patent and Trademark Office*